United States Patent
Kranz et al.

(10) Patent No.: US 6,547,757 B1
(45) Date of Patent: Apr. 15, 2003

(54) CATHETER

(75) Inventors: Curt Kranz, Berlin (DE); Max Schaldach, Erlangen (DE)

(73) Assignee: Biotronik Mess-und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 214 days.

(21) Appl. No.: 09/628,415

(22) Filed: Jul. 28, 2000

(30) Foreign Application Priority Data

Jul. 30, 1999 (DE) ......................................... 199 36 904

(51) Int. Cl.$^7$ ............................................. A61M 37/00
(52) U.S. Cl. ................. 604/95.04; 604/103.1; 604/523; 604/528; 600/478
(58) Field of Search ............................... 604/103.1, 523, 604/526, 528, 529, 270; 600/478, 433, 435

(56) References Cited

U.S. PATENT DOCUMENTS

| | | |
|---|---|---|
| 4,930,494 A | 6/1990 | Takehana et al. |
| 5,254,088 A | 10/1993 | Lundquist et al. |
| 5,273,535 A | 12/1993 | Edwards et al. |
| 5,284,138 A | 2/1994 | Kujawski |
| 5,364,351 A | 11/1994 | Heinzelman et al. |
| 5,622,170 A * | 4/1997 | Schulz ..................... 356/141.1 |
| 5,810,757 A * | 9/1998 | Sweezer et al. ............ 604/523 |
| 6,165,164 A * | 12/2000 | Hill et al. .................. 604/523 |
| 6,183,463 B1 * | 2/2001 | Webster, Jr. ................ 604/528 |

FOREIGN PATENT DOCUMENTS

| | | |
|---|---|---|
| DE | 3707787 | 9/1988 |
| DE | 197 50 850 C1 | 11/1997 |
| EP | 0 284 055 | 9/1988 |
| FR | 2 732 225 | 10/1996 |

* cited by examiner

*Primary Examiner*—Thomas Denion
*Assistant Examiner*—Jaime Corrigan
(74) *Attorney, Agent, or Firm*—Robert Kinberg; Venable, LLP.

(57) ABSTRACT

A catheter (10, 10', 10", 10'''), in particular for insertion into blood vessels of the human body, having at least one sensor (32) which is arranged at the distal end (12) of the catheter (10, 10', 10", 10''') and which is adapted to pick up a spacing signal which is dependent on the spacing of the sensor (32) with respect to the vessel wall, and control means (36, 36', 36") which are connected to the sensor for taking over the spacing signal.

16 Claims, 7 Drawing Sheets

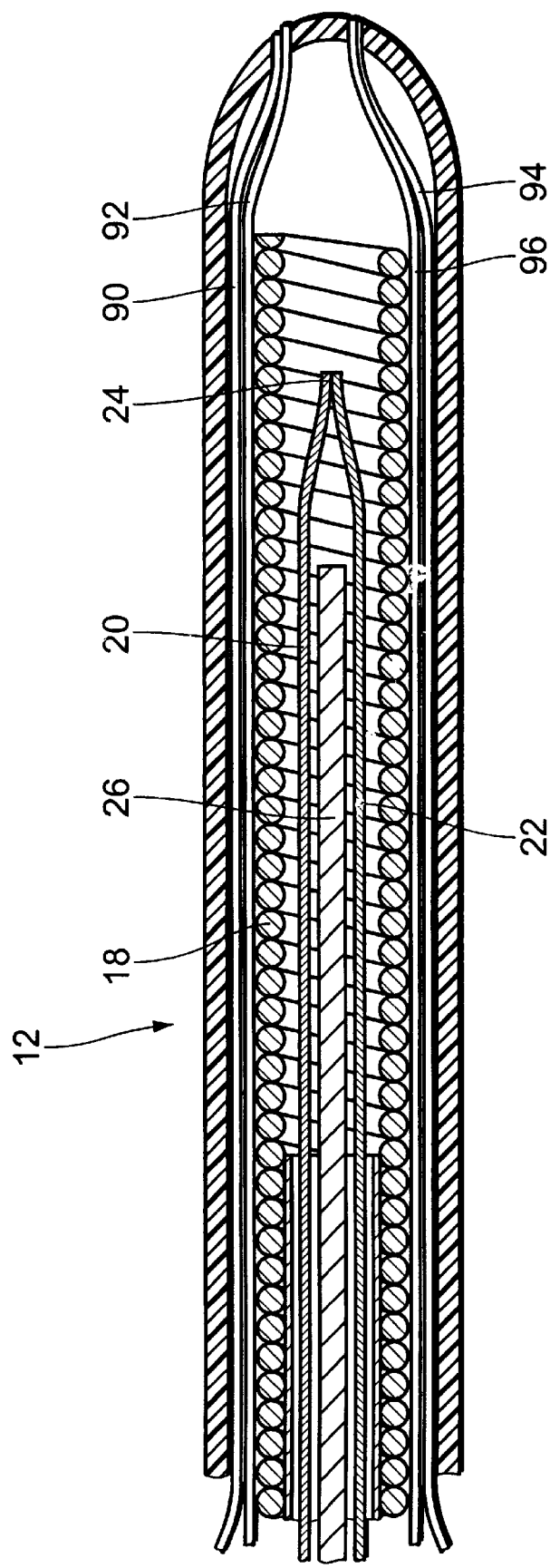
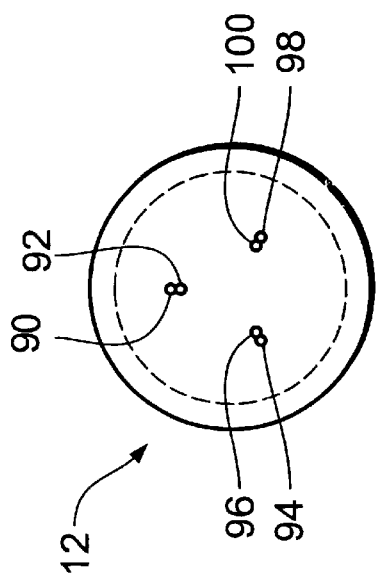
Fig. 6
Fig. 6a

CATHETER

CROSS-REFERENCE TO RELATED APPLICATION

Priority is claimed with respect to the application No. 199 36 904.6 filed in Germany on Jul. 30, 1999, the disclosure of which is incorporated herein by reference.

BACKGROUND OF THE INVENTION

The invention concerns a catheter, in particular for intravascular uses in the general sense. In the general sense as interpreted herein the term catheter is also intended to cover for example electrode lines which can be introduced through blood vessels into a heart, for cardiac pacemakers, ablation catheters and also guide wires. Guide wires serve in particular as an ancillary means for inserting catheters in the narrower sense or cardiac pacemaker electrode lines through blood vessels in the human body.

A large number of such catheters are known, for example ablation catheters and guide wires, which at the proximal end are provided with mechanical positioning or setting means in order to deflect the distal end into a desired direction, by suitable manual actuation of the setting means. In that way the guide wire can also be introduced manually through blood vessels involving angled configurations. The guide wire once introduced then serves as an ancillary means for the guided introduction of a catheter or an electrode line. In that case the catheter can be clipped in a portion-wise manner onto the guide wire. Alternatively the catheter can also be pushed over the guide wire. For that purpose such a catheter has a suitable lumen.

An ablation catheter which is controllable manually is known for example from U.S. Pat. No. 5,273,535. The catheter essentially comprises a gripping or handle element which goes into a catheter stem from which extends a flexible guide tube which terminates in a catheter tip with integrated electrode. Disposed at the end of the gripping element which is opposite to the catheter stem, is an electric line, by way of which the electrode is supplied with electrical energy.

Two draw wires which are secured to the tip of the catheter extend within the flexible guide tube. The draw wires are arranged in such a way that pulling on one draw wire or the other makes it possible to deflect the tip of the catheter in a first direction or a direction opposite to the first direction. The draw wires do not provide for the transmission of a pressure force. By virtue of deflection of the tip of the catheter and an additional rotary movement of the guide tube by means of the gripping element, the catheter can follow the curved configuration of a hollow organ in the body, without causing damage thereto.

The draw wires are movable alternately in a pulling mode by way of transmission means which are disposed in the gripping element and which are operated manually by a control element. The control element is here in the form of a control wheel. The transmission means convert the rotary movement of the control wheel into the pulling longitudinal movement for the draw wires. The transmission means comprise a shaft which is arranged stationarily and coaxially with respect to the control wheel and against which a respective draw wire bears from each of both sides. The two draw wires are secured to an apex point on the shaft. If now for example a rotary movement in the counterclockwise direction is effected at the control wheel, then the shaft also rotates in the counterclockwise direction and a wire is wound onto the shaft corresponding to the angle of rotation covered, and is thereby pulled. The other draw wire is correspondingly relieved of load. This involves a deflection movement of the tip of the catheter. Deflection in the opposite direction is produced in a similar manner by way of rotation of the control wheel in the clockwise direction. With this structure, the degree of deflection is established by the diameter of the shaft and is really slight by virtue of the structural boundary conditions involved.

Other manually controllable catheters are to be found in U.S. Pat. Nos. 5,254,088 and 5,364,351. Of those, U.S. Pat. No. 5,245,088 shows various alternative configurations of catheters, with a respective pair of control wires which are arranged in a lumen of the catheter so that it is possible to provide for lateral deflection of the distal end of the catheter by virtue of a relative movement of the control wires with respect to each other in their axial direction. The radial direction in which the deflection of the distal end of the catheter occurs can be adjusted by the control wires being rotated with respect to the rest of the catheter about a common longitudinal axis. Relative axial displacement of the control wires with respect to each other and rotation thereof with respect to the catheter casing can be effected by means of a hand control unit at the proximal end of the catheter.

SUMMARY OF THE INVENTION

Taking that state of the art as its basic starting point, the object of the invention is to provide a catheter which can be introduced more easily than known catheters in particular through blood vessels of the human body to a desired location, for example into a heart.

In accordance with the invention, that object is attained by a catheter having at least one sensor which is arranged at the distal end of the catheter and which is adapted to pick up a spacing signal dependent on the spacing of the sensor relative to the vessel wall, and control means which are connected to the sensor for taking over the spacing signal.

By virtue of the spacing signal being picked up directly at the distal end of the catheter, information about the position of the distal end of the catheter in for example a blood vessel is available at the control means without additional, for example extracorporal ancillary means. The corresponding spacing signal can be processed by virtue of the control means being of a suitable configuration to put it into any desired form and in particular can be used to control the deflection of the tip of the catheter, either manually or automatically. The invention therefore involves the realization of detecting the approach of the distal end of the catheter by sensor means and making available a suitable signal for controlling the deflection of the catheter, so that the distal end of the catheter upon approaching a vessel wall can be deflected in such a way that it moves away from the vessel wall.

In this connection, a particularly preferred catheter is one which is distinguished by actuators which are operatively connected to the control means and which are adapted to provide for deflection of the catheter, wherein the control means are adapted in response to a spacing signal from the sensors to generate a corresponding control signal for the actuators and pass it thereto in order to operate the actuators in such a way that the distal end of the catheter moves away from the vessel wall as a result of corresponding deflection by the actuators. Such a catheter enjoys the great advantage that with its distal end it maintains a spacing relative to the vessel walls, of its own accord, whenever possible, and therefore can be introduced into and passed through a blood vessel without complicated and intensive observation and manual control. The invention accordingly embraces the notion of combining a sensor for the spacing signal with suitable control means and actuators for deflection of the catheter to give an automatically operating system.

The actuators or the control means or both can in principle be arranged both at the distal end of the catheter and also at the proximal end thereof. For example piezoelectric actuators are suitable for the arrangement at the distal end.

In an alternative configuration of the invention a catheter can also be designed in such a way that the spacing signals detected by the sensor are displayed at the proximal end in order to simplify the known control of the catheter with manual setting means for deflection of the catheter. Accordingly a preferred catheter is also one which includes display means which are connected to the control means for actuation thereby.

Preferably, at least three sensors are arranged in a radially distributed array at the distal end of the catheter. In that way it is possible to obtain information about the direction of the approach of the catheter to a vessel wail and to counteract the approach movement by suitable operation of the actuators.

In addition, a preferred catheter is one whose sensor is an optical sensor or whose sensors include optical sensors. A particularly preferred alternative configuration of a catheter in that respect is one in which the sensor or sensors include light guides or optical fibers which end at the distal end of the catheter. In this case, the end of a light guide or optical fiber can itself serve as a sensor for light which impinges on the end of the optical fiber. Accordingly, a preferred catheter is one in which at least one of the optical fibers is adapted to receive light at the distal end of the catheter and transmit the received light to the control means. In that case, the received light represents the spacing signal. The catheter preferably has a further light guide or optical fiber which is adapted to output light at the distal end of the catheter and which preferably at the proximal end of the catheter is connected to a light source which outputs infrared light. The latter alternative configuration of the catheter is based on the realization that blood involves a transmission of about 90% in the infrared range between about 600 and 650 nm and is thus "transparent". In that way it is possible for infrared light to be caused to issue by way of the one optical fiber at the distal end of the catheter and for the strength of the infrared light reflected by the vessel walls to be returned as the spacing signal by way of other optical fibers to the proximal end of the catheter where either display values or control signals for corresponding actuators are derived from the spacing signal.

In connection with optical sensors, control means which are adapted to process optical signals are preferred.

As an alternative to the last-mentioned variant of the invention, it is also possible to provide control means which are adapted to process electrical signals. Accordingly alternatively preferred catheters are distinguished by a sensor or a plurality of sensors for outputting electrical signals. Such sensors can be capacitive proximity sensors which experience a change in their capacitance with an approach to a vessel wall. A spacing signal can then be derived from the attenuation of an electrical alternating current signal.

An alternatively preferred electrical sensor includes impedance detection means having at least two electrodes which are adapted to detect the impedance of blood flowing between the electrodes. Such a sensor makes use of the physical effect that, depending on the respective flow state, laminar or turbulent, which occurs according to the distance relative to the vessel wall, the blood involves a different level of conductance so that a spacing signal can be derived in that way.

A further alternative in respect of electrical sensors is represented by heatable thermistors whose electrical resistance varies with temperature. By virtue of the heating of the thermistors, the temperature thereof depends on how much heat is given off by the distal end of the catheter to the blood. That amount of heat however depends on the flow speed of the blood relative to the catheter. In that respect, the flow speed of the blood in the proximity of the vessel wall is lower than at a spacing from the vessel wall. Accordingly, the thermistor at a greater distance from the vessel wall is cooled to a greater degree so that the signal corresponding to the temperature of the thermistor can serve as a spacing signal.

In the case of a catheter provided with actuators and control means, the arrangement preferably has manual control means which are operatively connected to the actuators and which are designed in such a way that they permit a deflection of the catheter in a predeterminable fashion irrespective of the spacing signals which are passed from the sensors to the control means. In that way, automatic control of the catheter can be controlled by a manual control, in order for example in the case of vessel branchings to be able to specifically and targetedly predetermine a direction by hand.

BRIEF DESCRIPTION OF THE DRAWINGS

The invention will now be described in greater detail by means of embodiments with reference to the drawings in which:

FIG. 3a is a view in cross-section through the catheter of FIG. 3,

FIG. 6 shows the distal end of one of the catheters shown in FIGS. 1 through 3 with an optical spacing sensor, FIG. 6a is a plan view of the tip of the catheter shown in FIG. 6.

DETAILED DESCRIPTION OF THE INVENTION

Figures 1, 1A:
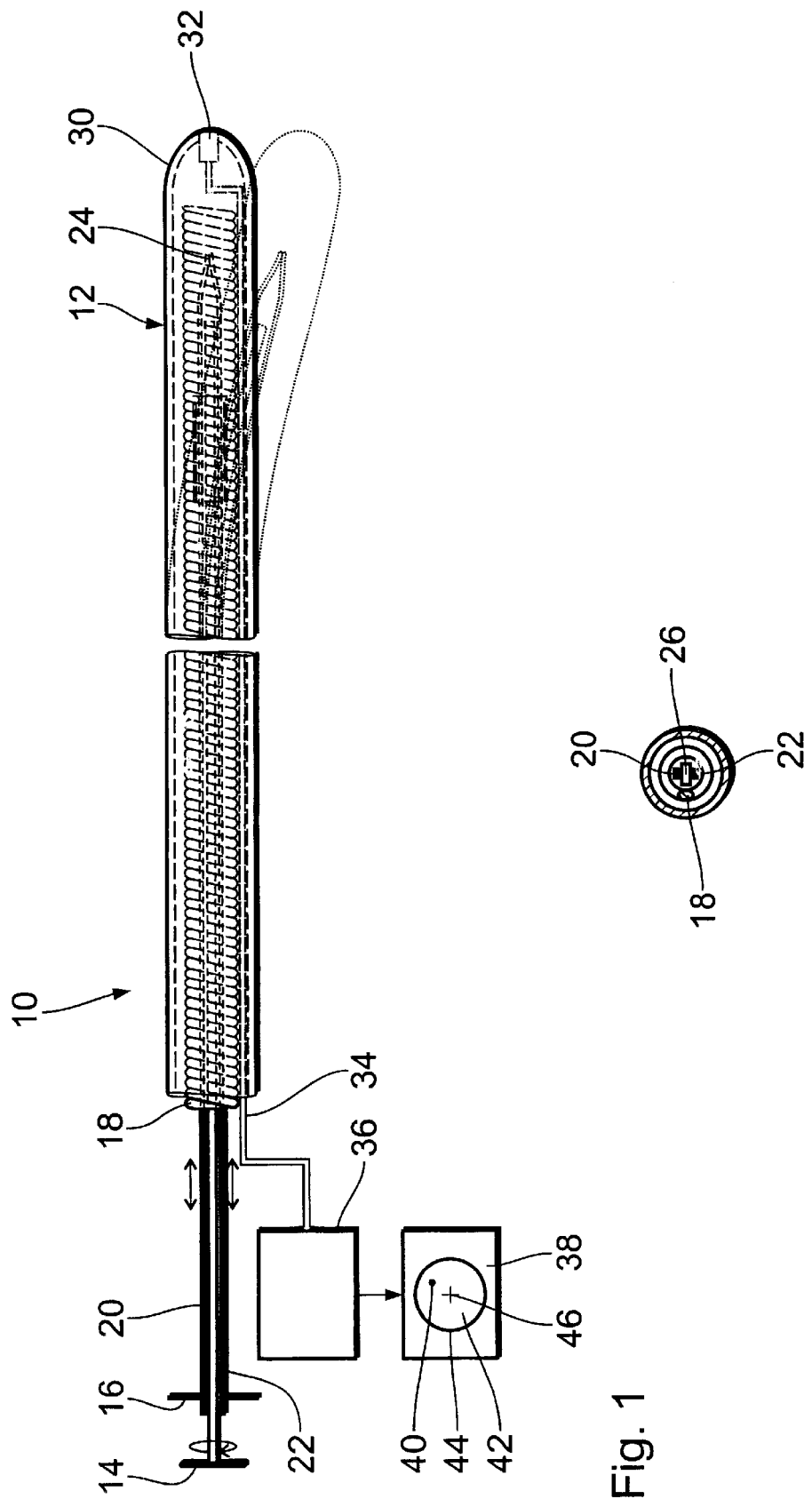
FIG. 1 shows a catheter according to the invention for manual control.
FIG. 1a is a view in cross-section through the catheter of FIG. 1.

FIG. 1 shows a catheter 10 whose distal end 12 is laterally deflectable by a deflection movement in any radial direction. This deflection movement is effected for example on the basis of the principle known from U.S. Pat. No. 5,254,088. For that purpose, at its proximal end, the catheter 10 has manual control means 14 and 16 which are connected to a spiral or coil casing 18 which encloses a lumen and which is flexible at its distal end, and two control wires 20 and 22 which are guided in the lumen of the spiral casing 18. The manual control means 16 are connected to the two control wires 20 and 22 in known manner in such a way that the wires are slidable relative to each other in the axial direction. At their distal ends 24 the two control wires 20 and 22 are connected together. Axial sliding movement of the control wires relative to each other causes lateral flexural deflection of the spiral casing 18 and thus the catheter 10 in the flexible region of the spiral casing 18 at the distal end 12 of the catheter 10.

The spiral casing 18 is arranged in the catheter 10 rotatably relative to the catheter 10. The radial direction of the lateral deflection movement which occurs upon deflection of the distal end 12 of the catheter can be determined by a rotational movement of the spiral casing 18 with the control wires 20 and 22 guided therein, with respect to the catheter 10. For that purpose, provided in the spiral casing 18 is a flat band or strip 26 which divides the lumen in the spiral casing 18 into two halves which each guide a respective one of the guide wires 20 and 22. The flat band or strip 26 is engaged at the distal end by the manual control means 14 in such a way that the flat band or strip 26 and therewith the guide wires 20 and 22 are rotatable relative to the rest of the catheter 10. The spiral casing 18 can be but does not necessarily have to be, rotated together with the flat band or strip 26 in the guide wires 20 and 22 relative to the rest of the catheter. The crucial consideration is the rotation of the guide wires 20 and 22. FIG. 1a is a sectional view of the spiral casing 18 with the control wires 20 and 22 arranged therein, and the flat band or strip 26.

Arranged in the region of the tip 30 of the catheter at the distal end 12 thereof is a spacing sensor 32 which is connected to a control unit 36 by way of a signal connection 34 illustrated in the form of a bus. The control unit 36 is in turn connected to a display unit 38. The control unit 36 generates control signals for the display unit 38, from spacing signals received from the spacing sensor 32. The spacing information in respect of the relative position of the catheter tip 30 between the walls for example of a blood vessel, such information being obtained from the spacing signals, is represented by the display unit 38 in such a way that a symbol 40 for the tip 30 of a catheter is represented in a display area 42 whose outer boundary 44 represents the wall of the blood vessel in which the tip 30 of the catheter is disposed and which includes a marking 46 for identifying the middle of the blood vessel.

By means of the information represented by way of the display unit 38, the tip 30 of the catheter can be controlled by means of the manual control elements 14 and 16 in such a way that as far as possible it is always in the middle of the vessel through which the tip 30 of the catheter is being passed. For that purpose, the symbol 40 representing the tip 30 of the catheter must be held in the display area 44 as much as possible in the proximity of the mark 46 representing the middle of the vessel. It will be appreciated that any desired deviations can be set by hand at any time in order for example to be able to introduce the tip of the catheter into vessel branchings.

Figure 2:
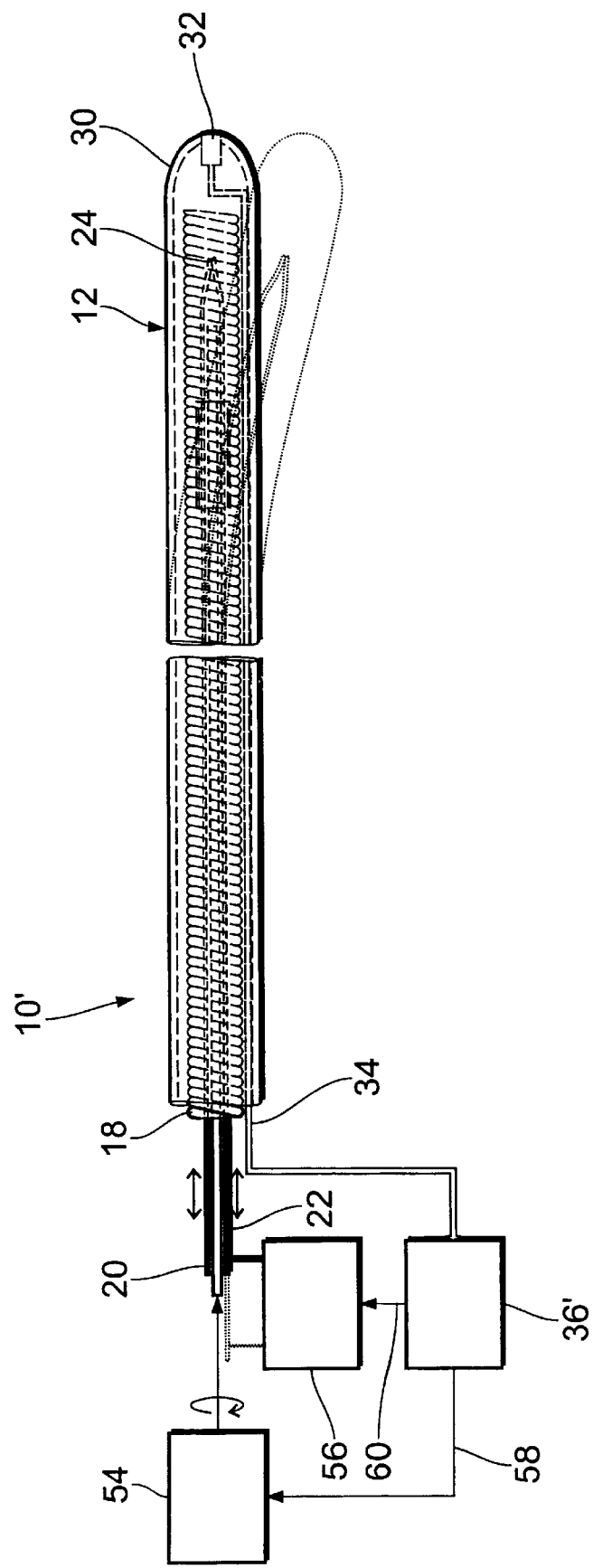
FIG. 2 shows a catheter suitable for automatic control.

FIG. 2 shows a catheter 10' which in terms of essential parts corresponds to that shown in FIG. 1. Identical parts are denoted by the same references as in FIG. 1. The essential differences between the catheter 10' in FIG. 2 and the catheter 10 in FIG. 1 are two mechanical control drives or actuators 54 and 56 for rotation of the guide wires 20 and 22 with respect to the rest of the catheter 10' and for the axial movement of the control wires 20 and 22 relative to each other. As in the case of the catheter 10 shown in FIG. 1, the control unit 36' is connected to the spacing sensor 32 by way of a signal connection 34. From the spacing signal received from the sensor 32, the control unit 36' generates control signals for the actuators 54 and 56, to which the control unit 36' is connected by way of suitable control lines 58 and 60. The control signals for the actuators 54 and 56 are generated on the basis of the spacing signal in such a way that, as it approaches a vessel wall, the tip 30 of the catheter is moved away from the vessel wall by deflection of the distal end 12 of the catheter 10', such deflection being produced by means of the actuators 54 and 56. The catheter 10' therefore represents a system which can be introduced into and passed through a blood vessel, without manual control.

Figure 3:
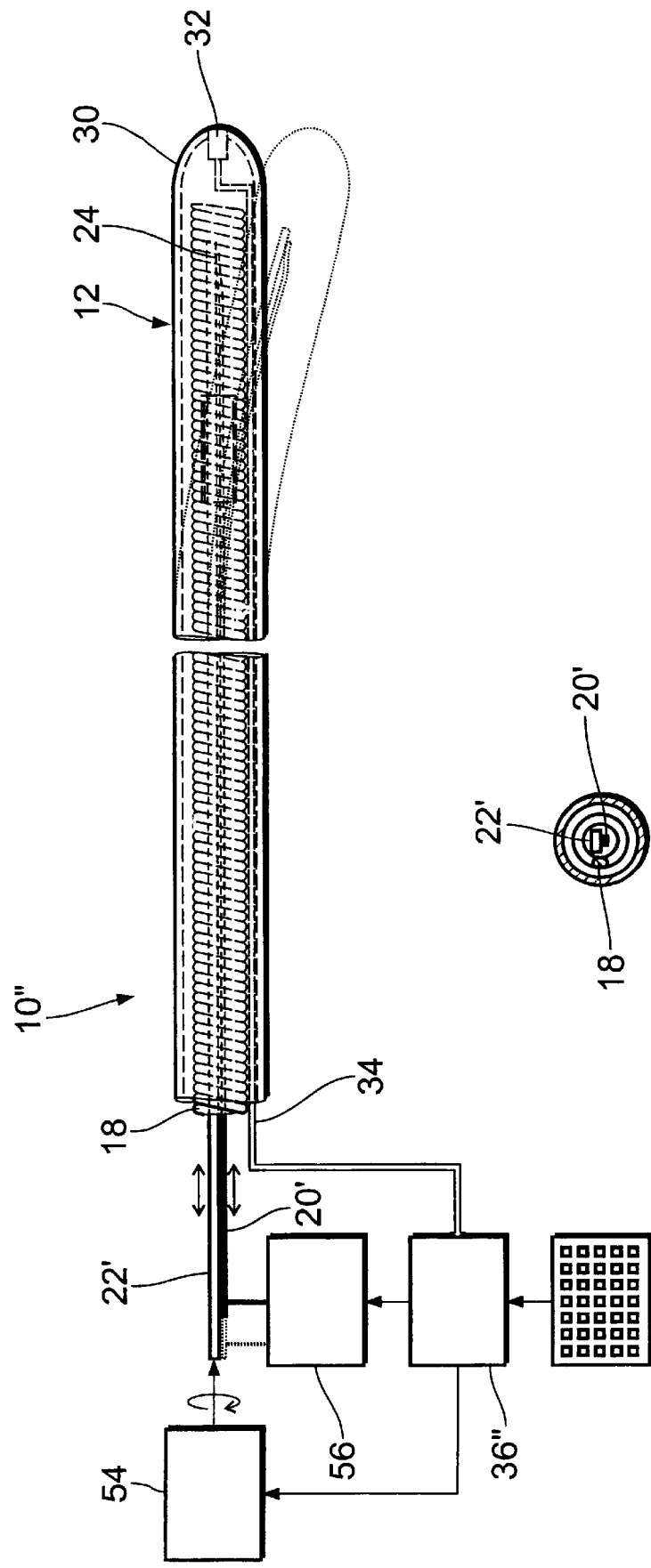
FIG. 3 shows a catheter suitable for manual and automatic control.

FIG. 3 shows a similar catheter to FIG. 2. In addition to the components already shown in FIG. 2, the catheter 10" in FIG. 3 has a manual control unit 62 with which the control signals for the actuators 54 and 56, which are obtained from the spacing signal from the spacing sensor 32, can be overridden in order deliberately and specifically to deflect the tip 30 of the catheter 10" by hand towards a vessel wall and to introduce the tip 30 of the catheter for example into a vessel branching disposed at that location. For that purpose, the manual control unit 62 is connected to the control unit 36". In addition, FIG. 3 shows a somewhat different structure in respect of the control wires 20' and 22' which are arranged in the lumen of the spiral casing 18. As can be seen from the sectional view in FIG. 3a, the wires are in the form of flat bands or strips and there is therefore no need to use an additional flat band or strip like that shown at 26 in FIGS. 1 and 2.

Figure 4:
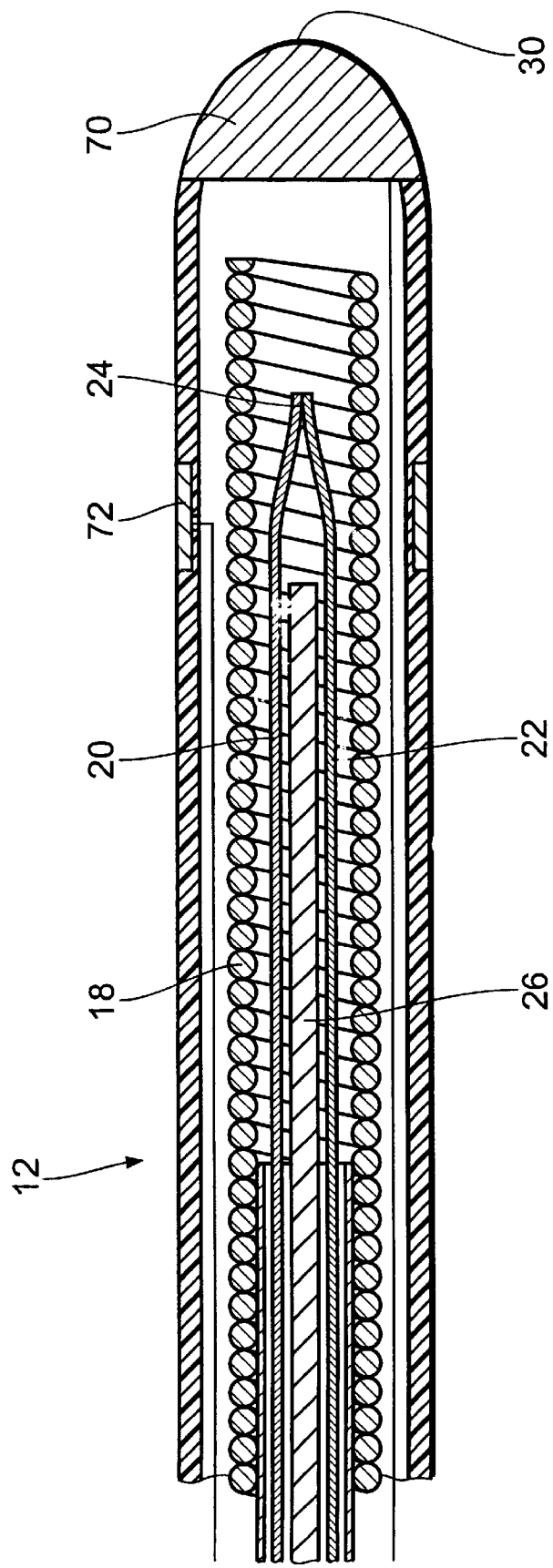
FIG. 4 shows the distal end of one of the catheters shown in FIGS. 1 through 3 with a first embodiment of an electrical spacing sensor.
Figure 5:
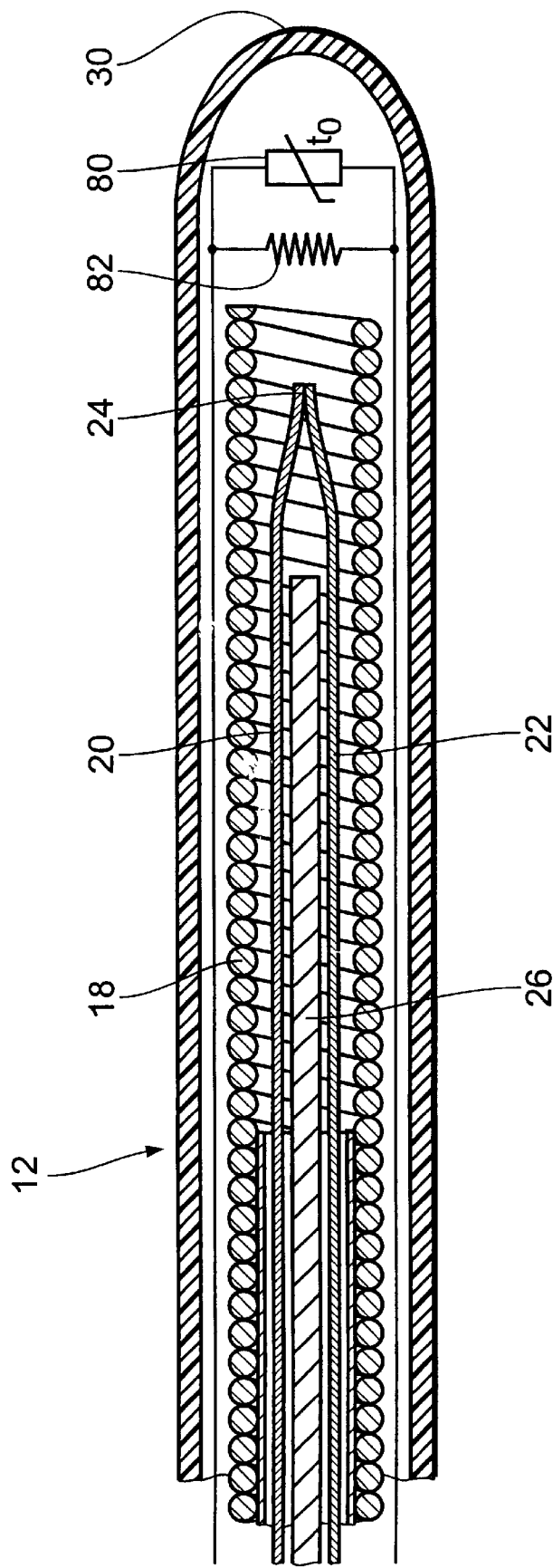
FIG. 5 shows the distal end of one of the catheters shown in FIGS. 1 through 3 with an alternative embodiment of an electrical spacing sensor.

The spacing sensor 32 of the catheters 10, 10' and 10" can be for example a capacitive spacing sensor. Alternative spacing sensors are shown in FIGS. 4 through 6. The distal end 12 of a catheter 10, which is illustrated in FIG. 4, is provided with two electrodes 70 and 72 of which the electrode 70 is in the form of a tip electrode at the tip 30 of the catheter while the electrode 72 is a ring electrode. The electrodes are connected by way of signal lines to the control unit 36, 36', 36" which is not shown in FIG. 4. The electrodes 70 and 72 can be used for capacitive spacing measurement or for measurement of the impedance of the blood between the electrodes. It is possible in that way to obtain a spacing signal, in the manner described hereinbefore.

In FIG. 5 the spacing sensor 32 is in the form a temperature-dependent resistor, that is to say a thermistor 80. The arrangement also includes a heating element 82 for heating the tip 30 of the catheter. A signal for the spacing of the tip 30 of the catheter relative to the vessel wall can be derived from cooling of the thermistor 80, in the manner described hereinbefore.

In the embodiment illustrated in FIG. 6 the spacing sensor 32 is an optical sensor. The spacing sensor 32 is formed by six light guides or optical fibers 90, 92, 94, 96, 98 and 100 which are respectively associated in pairs with each other. The pairs of optical fibers are uniformly distributed on a peripheral line in the region of the tip 30 of the catheter so that a respective one of the optical fibers of a pair preferably receives light which falls on a sector of the tip of the catheter, which is near the respective pair of optical fibers. This arrangement of the ends of the optical fibers 90, 92, 94, 96, 98 and 100 can be seen from the plan view of the tip 30 of the catheter in FIG. 6a.

Of the optical fibers which are associated with each other in paired relationship, one serves to pick up light signals and transmit same to a control unit which is suitable for processing optical signals. The respective other optical fiber associated with a pair of optical fibers is connected to an infrared light source (not shown) at the proximal end of the catheter 10 and passes light from that light source to the distal end of the catheter 10 where it issues at the end of the corresponding optical fibers and illuminates the corresponding area around the tip 30 of the catheter. Infrared light reflected by vessel walls is respectively picked up by the other optical fibers of a pair thereof and transmitted to the control unit where the light signal is compared to those of the other two light-receiving optical fibers of the other two pairs thereof. As blood in a wavelength range of between 600 and 650 nm has a transmission in the proximity of 90%, the strength of the received light signal depends on how close a pair of optical fibers is disposed to a vessel wall. A greater degree of reflection signifies closer proximity to the vessel wall. For comparison of the three light signals obtained in the above-described manner, in the control unit, it is easily possible to ascertain in which radial direction, relative to the catheter, the tip 30 of the catheter is approaching a vessel wall and can be suitably controlled in opposite relationship by way of the actuators. The three light-receiving optical fibers of the light signals going to the control unit in that case together form the spacing signal.

An alternative embodiment of the spacing sensor 32 which also operates with light guides or optical fibers and infrared light has only two light guides or optical fibers of which one emits light and the other receives light which is incident from the sides at the tip of the catheter 10 and passes same to the control unit. By virtue of transmission of the blood not being one hundred percent, the light signal as the spacing signal is at its weakest when the tip 30 of the catheter is in the middle of the vessel.

Figure 7:
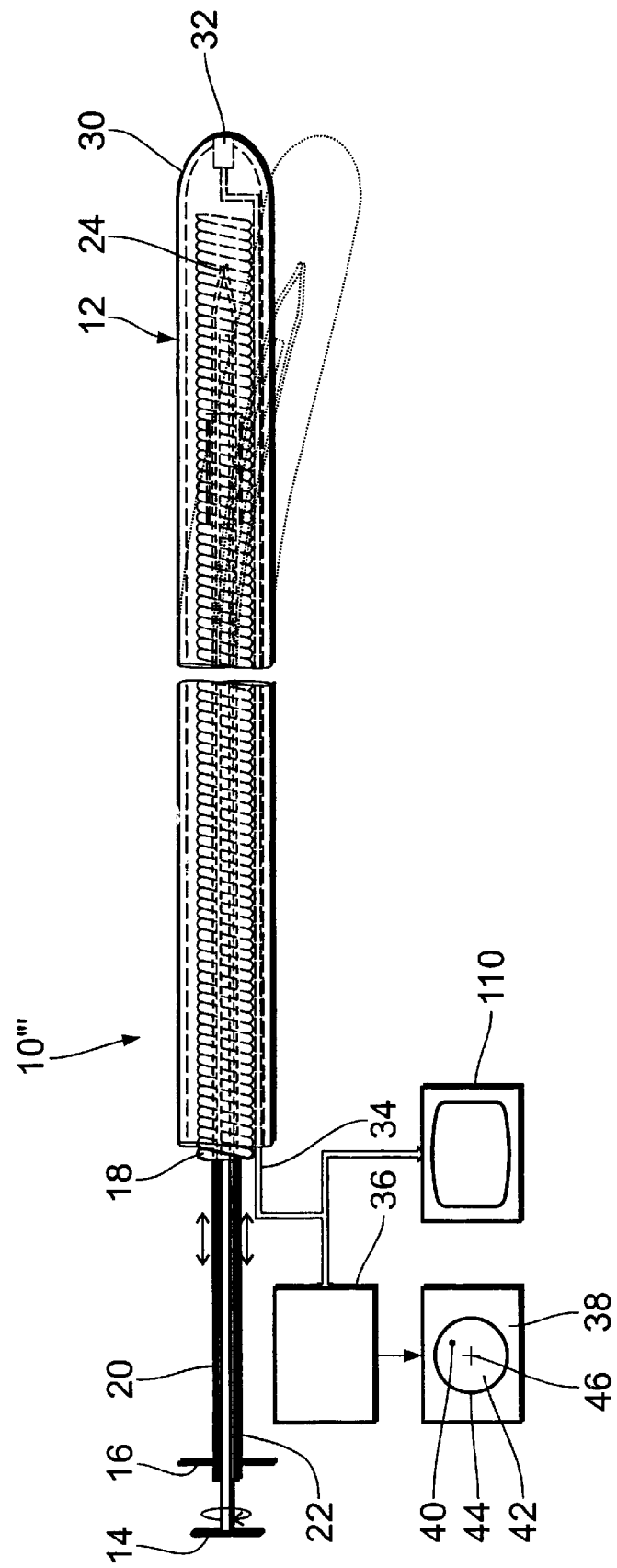
FIG. 7 shows a catheter similar to FIG. 1 with a display unit for a quasi-endoscopically obtained image.

The catheter 10''' in FIG. 7, in addition to the catheter 10 shown in FIG. 1, has a display unit 110 which is connected to the sensor 32. In this case the sensor 32 is in the form of an optical, imaging sensor. The image which is picked up-by the sensor 32 is represented by the display unit 110. The catheter 10''' thereby practically becomes an endoscope-like unit. The information obtained by means of the sensor 32 and represented by the display unit 110 can be used in particular for suitably positioning the catheter. With such a catheter it is possible to look for suitable electrode placements or suitable ablation locations if the catheter is an ablation catheter.

What is claimed is:

1. A catheter for insertion into a blood vessel of a human body, the catheter including at least one sensor arranged at a distal end of the catheter and adapted to pick up a spacing signal dependent on the spacing of the sensor with respect to the vessel wall; and control means connected to the sensor for producing a control signal in dependence of the spacing signal.

2. The catheter according to claim 1, further including actuators operatively connected to the control means and responsive to the control signal for deflecting the distal end of the catheter away from the vessel wall.

3. The catheter according to claim 2, further including manual control means operatively connected to the actuators for deflecting the catheter in a predeterminable manner independently of the spacing signal passed from the at least one sensor to the control means.

4. The catheter according to claim 1, further comprising display means connected to the control means and presenting a display representing the spacing signal.

5. The catheter according to claim 1, wherein the at least one sensor includes three sensors arranged in a radial distribution at the distal end of the catheter.

6. The catheter according to claim 1, wherein the at least one sensor comprises an optical sensor.

7. The catheter according to claim 6, wherein the optical sensor includes light guides which end at the distal end of the catheter.

8. The catheter according to claim 7, wherein one of the light guides comprises an output light guide for outputting light at the distal end of the catheter.

9. The catheter according to claim 8, further including a light source for outputting infrared light, and wherein the output light guide is coupled at a proximal end of the catheter to the light source.

10. The catheter according to claim 7, wherein at least one of the light guides is adapted to receive light at the distal end of the catheter and to transmit the received light to the control means.

11. The catheter according to claim 6, wherein the control means is adapted for processing optical signals.

12. The catheter according to claim 1, wherein the control means is adapted for processing electrical signals.

13. The catheter according to claim 12, wherein the at least one sensor comprises a capacitive proximity sensor.

14. The catheter according to claim 12, wherein the at least one sensor comprises impedance detection means having at least two electrodes for detecting an impedance of blood between the electrodes.

15. The catheter according to claim 1, further comprising display means connected to the at least one sensor for displaying information picked up from the at least one sensor.

16. The catheter according to claim 15, wherein the at least one sensor is an optical sensor and the display means is connected to the optical sensor for displaying at least one image picked up by the optical sensor.

* * * * *